(12) United States Patent
Karvinen et al.

(10) Patent No.: US 8,178,729 B2
(45) Date of Patent: May 15, 2012

(54) HYDROFORMYLATION PROCESS

(75) Inventors: Esko Karvinen, Helsinki (FI); Juha Lehtonen, Porvoo (FI); Joni Kunnas, Sipoo (FI); Merja Harteva, Espoo (FI)

(73) Assignee: Perstorp Specialty Chemicals AB, Perstorp (SE)

( * ) Notice: Subject to any disclaimer, the term of this patent is extended or adjusted under 35 U.S.C. 154(b) by 838 days.

(21) Appl. No.: 11/908,780

(22) PCT Filed: Mar. 15, 2006

(86) PCT No.: PCT/SE2006/000329
§ 371 (c)(1),
(2), (4) Date: May 2, 2008

(87) PCT Pub. No.: WO2006/098685
PCT Pub. Date: Sep. 21, 2006

(65) Prior Publication Data
US 2008/0281128 A1    Nov. 13, 2008

(30) Foreign Application Priority Data

Mar. 16, 2005   (SE) ...................................... 0500590

(51) Int. Cl.
*C07C 45/50* (2006.01)
(52) U.S. Cl. ....................................... 568/451; 568/454
(58) Field of Classification Search .................. 568/451, 568/454

See application file for complete search history.

(56) References Cited

FOREIGN PATENT DOCUMENTS

WO     WO 02/20448    *   3/2002

* cited by examiner

*Primary Examiner* — Sikarl Witherspoon
(74) *Attorney, Agent, or Firm* — Novak Druce + Quigg LLP

(57) ABSTRACT

Disclosed is a process for hydroformylation of α-olefin wherein said α-olefin is reached with carbon monoxide or carbon monoxide and hydrogen and/or a reducing agent in presence of a catalyst complex based on a rhodium precursor and a ligand mixture comprising at least 1% by weight of trphenylphosphine and at least 5% by weight of diphenylcyclohexylphosphine, tris-(o-tolyl)phosphine, tris-(p-tolyl) phosphine or (2-methyl-phenyl)diphenylphospine.

20 Claims, No Drawings

HYDROFORMYLATION PROCESS

The present invention relates to a process for hydroformylation of an α-olefin in the presence of a rhodium catalyst complex based on two different ligands and a rhodium precursor. In particular, the invention concerns a process for hydroformylation of an α-olefin having three or more carbon atoms in its main carbon chain, which process exhibits improved iso-selectivity. In further aspects, the present invention refers to a catalyst complex based on a rhodium precursor and two different ligands and to the use of said catalyst complex in hydroformylation of an α-olefin.

Hydroformylation is the general term applied to the reaction of an olefinic substrate with carbon monoxide and hydrogen and/or a reducing agent to form aldehydes having one carbon atom more than the original olefinic reactant as illustrated by Scheme 1 below.

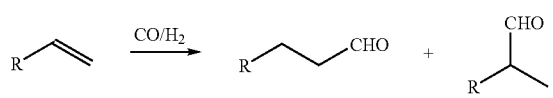

wherein R is a hydrocarbyl residue optionally comprising functional groups, such as carboxyl, hydroxyl and/or ester groups.

One of the most important industrial applications for hydroformylation processes is the so called oxo process, that is hydroformylation of olefins in the presence of transition-metal catalyst complexes. Yielded aldehydes can for instance be hydrogenated to give so called oxo alcohols and long-chain products can be converted into sulphonates and used as detergents. The oxo process was discovered in 1938 by Roelen and co-workers of Ruhr Chemie. The first catalysts, and still used on a large scale, were cobalt carbonyl complexes formed from $[HCo(CO)_4]$. The process is carried out at temperatures of 120-175° C. and pressures of several hundred atm. The high pressures are required to maintain the cobalt in the form of a soluble metal carbonyl complex. Use of cobalt complexes with phosphine ligands led to processes with improved selectivities. A significant advance in hydroformylation technology was made with the discovery that phosphine complexes of rhodium, similar to those used in the Wilkinson hydrogenation, but incorporating H, CO and olefinic ligands as well as triphenylphosphine, have catalytic activities several times higher than cobalt complexes. Furthermore, the rhodium complexes are stable enough to be used at low pressures, typically 1.5 MPa (15 atm) at a reaction temperature of about 90° C. Extensive research has been made on rhodium phosphine complexes bonded to solid supports, but the resulting catalysts were not sufficiently stable as rhodium leached into the reaction mixture. A more successful solution to the engineering problem resulted from the application of a two-phase liquid-liquid process. Hydroformylation and the oxo process are further disclosed and discussed in for instance Kirk-Othmer *Encyclopedia of Chemical Technology*, 4$^{th}$ ed. vol. 17, chapter "*Oxo Process*" and in *Applied Homogeneous Catalysis with Organometallic Compounds—A Comprehensive Handbook in Two Volumes*, chapter 2.1.1. pages 29-102, "*Hydroformulation (Oxo Synthesis, Roelen Reaction)*".

If the olefin chain contains more than two carbon atoms, hydroformylation results in a mixture of linear and branched aldehydes, and a key issue in the hydroformylation reaction is how to control the ratio of normal to branched (iso) products. In case of linear olefins the normal product is usually the desired one, while in functional or asymmetric hydroformylation the end application determines the desired product form. Branched (iso-form) hydroformylation compounds are of particular interest as starting materials for fine and specialty chemicals, such as sterically hindered polyols. Generally, the reaction conditions and the specific catalyst system used have a great effect on the chemical structure of the hydroformylation product and product distribution. In the late 70's, Tanaka et al., *Bull. Chem. Soc. Jpn.*, 50 (1979) 9, 2351-2357, studied the effect of shorter methylene chained diphosphines in combination with $Rh_2Cl_2(CO)_4$ catalyst on product selectivity in hydroformylation. The use of triphenylphosphine ligands suppressed the hydrogenation and increased the isomer content, but the branched (iso) to normal ratio (i/n-ratio) was still unsatisfactorily low.

Various regioselective hydroformylation processes have been suggested since Tanaka published his work. WO 93/14057 discloses a process wherein an olefin is reacted with carbon monoxide in the presence of a soluble catalyst comprising a rhodium complex and a bidentate phosphine ligand. Branched aldehydic esters are, using unsaturated olefins as reactants, produced in good yield and high selectivity. U.S. Pat. No. 5,364,970 suggests using a catalyst system based on inorganic rhodium precursors and various phosphorous, arsenic or antimony atom containing ligands for increased selectivity and reaction rates of the desired α-formyl isomers in hydroformylation of unsaturated carbonyl compounds. N. Rosas et al, *Revista Latino Amer. Quim.*, 8, 121-122 (1977), disclose catalytic hydroformylation of ethylene using several chlorine containing rhodium derivatives of general formula $Rh(CO)ClL_n$, wherein L is triarylphosphine, triphenyl, tri-p-methylphenyl, tri-o-methylphenyl, tri-p-methyloxyphenyl or tri-o-methyloxyphenyl. U.S. Pat. No. 4,945,185 teaches a hydroformylation process for producing an aldehyde or a mixture of a ketone and an aldehyde by the reaction over an acid containing rhodium catalyst, obtained by forming a reaction mixture comprising a catalytic amount of a catalyst complex consisting of rhodium complexed with a triorganophosphine and a carboxylic acid having a phenyl group substituted in the para position with an electron-withdrawing group.

In spite of prior efforts there still exists a need for further improving the catalytic activity as well as the regio and chemoselectivity expressed as for instance iso-selectivity. Surprisingly it has now been found that a substantially improved iso-selectivity with a similar or even improved α-olefin conversion in hydrogenation of α-olefins can be obtained by using a catalyst complex based on a combination of two different ligands and at least one rhodium precursor. In the process of the present invention, which utilises a mixture of two ligands, the i/n-ratio, such as the ratio between for instance iso-butyric aldehyde and n-butyric aldehyde yielded in a hydroformylation of propene, the most preferred α-olefin, can easily be controlled within an i/n-ratio of for instance 1:1 and 1:6. Accordingly, the present invention refers to a process, such as a continuos process, for hydroformylation of an α-olefin, such as an α-olefin having two or preferably three or more carbon atoms in its main carbon chain, which hydroformylation is carried out in the presence of a catalyst complex based on at least one rhodium precursor and a mixture of two different ligands. The process of the present invention results in a substantially improved iso-selectivity to a degree which by no means can be predicted from prior art hydroformylation processes and/or catalysts, such as catalyst complexes.

Preferred α-olefins are, in various embodiments of the present invention, suitably selected from the group consisting of ethylene, propene, butenes, pentenes and hexenes or a mixture thereof or therewith. The olefinic feedstock can contain one or several of above listed α-olefins. In case of ethylene, only normal aldehyde (propionaldehyde) is possible and it is therefore typically used only as co-feed with at least one other α-olefin as listed above.

Said catalyst complex is based on a ligand mixture comprising at least 1% by weight of triphenylphosphine and at least 5%, such as 10%, by weight of diphenylcyclohexylphosphine, tris-(o-tolyl)phosphine, tris-(p-tolyl)phosphine or (2-methylphenyl)diphenylphosphine and at least one rhodium precursor. The structures of above said ligands can be illustrated by appended Formulas I-V.

The catalyst complex used in the hydroformylation process according to the present invention is suitably prepared by reacting a rhodium compound with a said ligand mixture to form a reactive complex at suitable reaction conditions. The rhodium concentration can vary substantially depending on the desired catalyst properties and the application. A preferred rhodium concentration is, however, 20-1000, such as 50-500, ppm by weight of obtained reaction mixture and a preferred ligand concentration is 1-15% by weight of the reaction mixture.

The rhodium precursor used is either a rhodium salt or an organometal compound, such as a halogenide, a nitrate, a carbonyl compound, a sulphate, an acetate, a dicarbonyl-acetylacetonate. Specific examples of suitable precursors include rhodium(III)nitrate, rhodium(I)acetate, acetylacetonatedicarbonyl rhodium(I), di(rhodium)tetracarbonyl dichloride, dodecancarbonyltetrarhodium and hexadecancarbonylhexarhodium.

Said hydroformylation can, in principle, be carried out by methods known per se. Thus, the α-olefin is reacted with either a syngas comprising carbon monoxide or carbon monoxide and hydrogen and/or a reducing agent in the presence of said catalyst complex. Said syngas with which the α-olefin is reacted comprises in preferred embodiments of the present invention hydrogen and carbon monoxide at a molar ratio hydrogen to carbon monoxide of for instance 0.1:2.5, such as 0.8:1.2, 1.0:1.1 or 1:1.

The hydroformylation process of the present invention is preferably carried out at remarkably mild conditions. The preferred temperature range is 30-200° C., such as 50-130° C. or 80-120° C. and the preferred reaction pressure is 1-150 bar, such as 5-50 or 10-30 bar.

The process of the present invention is in its most preferred embodiments a hydroformylation of propene performed at a temperature of 80-120° C., a pressure of 10-30 bar, a molar ratio hydrogen to carbon monoxide of 0.1:2.5, a concentration of ligands of 1-15% by weight of the reaction mixture and a rhodium concentration of 20-1000, such as 50-500, ppm by weight of the reaction mixture.

In a further aspect, the present invention refers to a catalyst complex as disclosed above, that is a catalytically active complex based on at least one rhodium precursor and a ligand mixture comprising at least 1% by weight of triphenylphosphine and at least 5%, such as 10%, by weight of diphenylcyclohexylphosphine, tris-(o-tolyl)phosphine, tris-(p-tolyl)phosphine or (2-methylphenyl)diphenylphosphine. Said rhodium precursor is preferably a halogenide, a nitrate, a carbonyl compound, a sulphate, an acetate or a dicarbonyl-acetylacetonate, such as rhodium(III)nitrate, rhodium(I)acetate, acetylacetonatedicarbonyl rhodium(I), di(rhodium)tetra-carbonyl dichloride, dodecancarbonyltetrarhodium or hexadecancarbonylhexarhodium. Said catalyst complex is primarily intended for hydroformylations of α-olefins and is preferably formed in situ, during such a hydroformylation.

In yet a further aspect, the present invention refers to the use of said catalyst complex in a hydroformylation of an α-olefin, such as ethylene, propene, a butene, a pentene or a hexene or a mixture thereof or therewith. Ethylene is typically used a co-feed with at least one other α-olefin as listed above. Said hydroformylation is preferably performed at a ligand concentration of 1-15% by weight of the reaction mixture and a rhodium concentration of 20-1000 ppm by weight of obtained reaction mixture.

Without further elaboration, it is believed that one skilled in the art can, using the preceding description, utilise the present invention to its fullest extent. In the following Examples 1-4 and 6-7 refer to hydroformylations according to embodiments of the present invention. Examples 5 and 8 are a comparative Examples of a single ligand hydroformylation outside the scope of the present invention. Tables 1 and 2 present results obtained by GC analyses of the products obtained in Examples 1-8. All parts given in Examples 1-8 are parts by weight.

EXAMPLE 1

39.08 parts of 2,2,4-trimethyl-1,3-pentanediol mono-iso-butyrate (Nx 795™, Perstorp Oxo AB, Sweden), 1.01 parts of the ligand triphenylphosphine (TPP), 4.13 parts of the ligand diphenylcyclohexylphosphine (CP) and 0.033 parts of the rhodium precursor acetylacetonatedicarbonyl rhodium(I) dissolved in 8.04 parts of Nx795 were charged in a stainless steel autoclave. In order to remove oxygen from the system, the reactor was under agitation flushed with nitrogen for 3 minutes. 1.5 parts of propene was charged to the reactor and a zero sample was withdrawn. Agitation and heating was now commenced. Charging of syngas, $H_2$ and CO at a molar ratio 1:1, was initiated when a reaction temperature of 100° C. was reached. The total pressure of the system was 11 bar. A samples was withdrawn after 3 hours of reaction and analysed by GC with regard to propene conversion to butyric aldehydes and selectivity to iso-butyric aldehyde (iso-selectivity). The result is given in Table 1.

EXAMPLE 2

Example 1 was repeated with the difference that 4.73 parts of the ligand tris-(o-tolyl)phosphine (TOTP) was charged instead of 4.13 parts of the ligand diphenylcyclohexylphosphine (CP). Propene conversion to butyric aldehydes and selectivity to iso-butyric aldehyde (iso-selectivity) after 3 hours of reaction are given in Table 1.

EXAMPLE 3

Example 1 was repeated with the difference that 4.37 parts of the ligand (2-methylphenyl)-diphenylphosphine (MeP) was charged instead of 4.13 parts of the ligand diphenylcyclohexylphosphine (CP). Propene conversion to butyric aldehydes and selectivity to iso-butyric aldehyde (iso-selectivity) after 3 hours of reaction are given in Table 1.

EXAMPLE 4

Example 1 was repeated with the difference that 1.72 parts of the ligand triphenylphosphite (TPP), 0.5 parts of the ligand tris-(p-tolyl)phosphine (TPTP) was charged instead of 1.01 parts of the ligand triphenylphosphine (TPP) and 4.13 parts of the ligand diphenylcyclo-hexylphosphine (CP). Propene conversion to butyric aldehydes and selectivity to iso-butyric, aldehyde (iso-selectivity) after 3 hours of reaction are given in Table 1.

EXAMPLE 5

Comparative 43.61 parts of 2,2,4-trimethyl-1,3-pentanediol mono-iso-butyrate (Nx 795™, Perstorp Oxo AB, Sweden), 2.37 parts of the ligand triphenylphosphine (TPP) and 0.013 parts of the acetylacetonatedicarbonyl rhodium(I) dissolved in 4.02 parts of Nx795 were charged in a stainless steel autoclave. In order to remove oxygen from the system, the reactor was under agitation flushed with nitrogen for 3 minutes. 1.6 parts of propene was charged to the reactor and a zero sample was withdrawn. Agitation and heating was now commenced. Charging of syngas, $H_2$ and CO at a molar ratio 1:1, was initiated when a reaction temperature of 100° C. was reached. The total pressure of the system was 11 bar. A samples was withdrawn after 3 hours of reaction and analysed by GC with regard to propene conversion to butyric aldehydes and selectivity to iso-butyric aldehyde (iso-selectivity). The result is given in Table 1.

EXAMPLE 6

82.25 parts of 2,2,4-trimethyl-1,3-pentanediol mono-iso-butyrate (Nx 795™, Perstorp Oxo AB, Sweden), 12.19 parts n-butyraldehyde, 4.0 parts of the ligand triphenylphosphine (TPP), 1.5 parts of the ligand tris-(p-tolyl)phosphine (TPTP) and 0.0627 parts of the rhodium precursor acetylacetonatedicarbonyl rhodium(I) were charged to a continuous reactor system. The catalyst solution was now circulated in the system (with the help of a piston pump) and when the temperature of the reactor was 60-70° C., the feed of propene, syngas ($H_2$/CO=1/1 mole/mole) and nitrogen was commenced. The reactor was equipped with a four-bladed turbine and baffles. The reactor operated at 96° C. and 15 bar and the agitation speed was 650 rpm. From the reactor the catalyst solution, product and gases went to a flash vessel separating unreacted gases from the product and catalyst solution. The flash vessel operated at 20° C. The product was separated from the catalyst solution in a separation reactor operating at 120° C. The catalyst solution was re-circulated to the reactor with the help of a piston pump. The product vessel was emptied every day and the amount of product was weighed and analysed by GC. From the top of the flash vessel a gas sample was taken every week day and analysed by GC. The result is given in Table 2.

EXAMPLE 7

Example 6 was repeated with the difference that 2.0 parts of the ligand diphenylcyclo-hexylphosphine (CP), 5.39 parts of the ligand triphenylphosphine (TPP) was charged instead of 4.0 parts of the ligand triphenylphosphine (TPP) and 1.5 parts of the ligand tris-(p-tolyl)phosphine (TPTP). The result is given in Table 2.

EXAMPLE 8

Comparative 71.97 parts of 2,2,4-trimethyl-1.3-pentanediol mono-iso-butyrate (Nx 795™, Perstorp Oxo AB, Sweden), 15.36 parts n-butyraldehyde, 12.61 parts of the ligand triphenylphosphine (TPP) and 0.0627 parts of the rhodium precursor acetylacetonatedicarbonyl rhodium(I) were charged to a continuous reactor system. The catalyst solution was circulating in the system (with the help of a piston pump) and when the temperature of the reactor was 60-70° C., the feed of propene, syngas ($H_2$/CO=1/1 mole/mole) and nitrogen was commenced. The reactor set-up, reaction conditions and sampling were as in Example 6 and 7. The result is given in Table 2.

TABLE 1

| Example | Ligand(s) | Propene Conversion, % | Iso-selectivity, % by weight |
|---|---|---|---|
| 1 | TPP/CP | 99.7 | 27.5 |
| 2 | TPP/TOTP | 99.5 | 24.0 |
| 3 | TPP/MeP | 99.5 | 24.5 |
| 4 | TPP/TPTP | 99.4 | 25.8 |
| 5 (Comparative) | TPP | 98.4 | 14.5 |

TABLE 2

| Example | Ligand(s) | Iso-selectivity after 2 days, % by weight | Iso-selectivity after 15 days, % by weight |
|---|---|---|---|
| 6 | TPP/TPTP | 18.7 | 19.9 |
| 7 | TPP/CP | 18.0 | 21.7 |
| 9 (Comparative) | TPP | 14.2 | 16.5 |

TPP = Triphenylphosphine
CP = Diphenylcyclohexylphosphine
TOTP = Tris-(o-tolyl)phosphine
MeP = (2-Methylphenyl)diphenylphosphine
TPTP = Tris-(p-tolyl)phosphine Formulas I-V

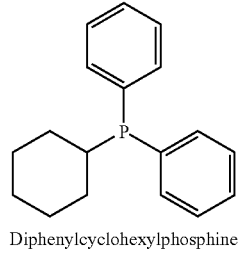

Diphenylcyclohexylphosphine

Formula I

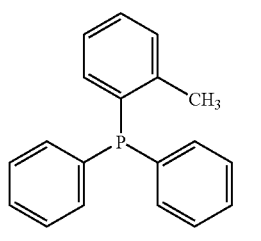

(2-Methylphenyl)-diphenylphosfine

Formula II

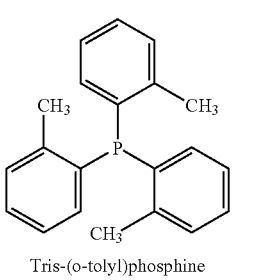

Tris-(o-tolyl)phosphine

Formula III

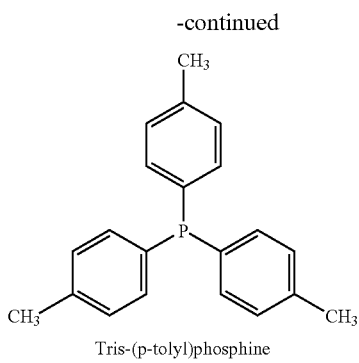

Tris-(p-tolyl)phosphine

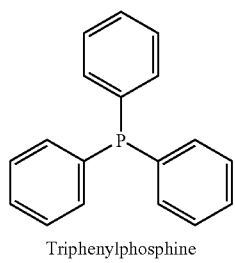

Triphenylphosphine

The invention claimed is:

1. A hydroformylation process with increased iso-selectivity, wherein an α-olefin is reacted with carbon monoxide or carbon monoxide and hydrogen and/or a reducing agent in presence of a catalyst complex based on a rhodium precursor and a ligand system, said catalyst complex being based on at least one rhodium precursor and a ligand mixture comprising at least 1% by weight of triphenylphosphine and at least 5% by weight of diphenylcyclohexylphosphine, tris-(o-tolyl)phosphine, tris-(p-tolyl)phosphine, or (2-methylphenyl)diphenylphosphine.

2. The process according to claim 1, wherein said α-olefin is selected from the group-consisting of ethylene, propene, a butene, a pentene, a hexane and mixtures thereof.

3. The process according to claim 1, wherein said α-olefin is a mixture of propene and ethylene.

4. The process according to claim 1, wherein said α-olefin is propene.

5. The process according to claim 1, wherein said hydroformylation is performed at a ligand concentration of 1-15% by weight of the reaction mixture.

6. The process according to claim 1, wherein said hydroformylation is performed, at a rhodium concentration of 20-1000, ppm by weight of obtained reaction mixture.

7. The process according to claim 1, wherein said rhodium precursor is a halogenide, a nitrate, a carbonyl compound, a sulphate, an acetate or a dicarbonyl acetylacetonate.

8. The process according to claim 1, wherein said rhodium precursor is rhodium(III)nitrate, rhodium(I)acetate, acetylacetonatedicarbonyl rhodium(I), di(rhodium)tetracarbonyl dichloride, dodecancarbonyltertrarhodium or hexadecancarbonylhexarhodium.

9. The process according to claim 1, wherein said catalyst complex is formed in situ in said hydroformylation.

10. The process according to claim 1, wherein said hydroformylation is performed at a temperature of 30-200° C.

11. The process according to claim 1, wherein said hydroformylation is performed at pressure of 1-150 bar.

12. A process according to claim 1 wherein said α-olefin is reacted with a syngas comprising hydrogen and carbon monoxide at a molar ratio of hydrogen to carbon monoxide of 0.1:2.5.

13. The process according to claim 1, wherein said hydroformylation is performed as a continuous process.

14. The process according to claim 1, wherein said hydroformylation is performed at a temperature of 50-130° C.

15. The process according to claim 1, wherein said hydroformylation is performed at a temperature 80-120° C.

16. The process according to claim 1, wherein said hydroformylation is performed at a temperature of 5-50 bar.

17. The process according to claim 1, wherein said hydroformylation is performed at a temperature of 10-30 bar.

18. The process according to claim 1, wherein said α-olefin is reacted with a syngas comprising hydrogen end carbon monoxide at a molar ratio of hydrogen to carbon monoxide ratio of 0.8:1.2.

19. The process according to claim 1, wherein said α-olefin is reacted with a syngas comprising hydrogen and carbon monoxide at a molar ratio of hydrogen to carbon monoxide of 1.0:1.1.

20. The process according to claim 1, wherein said α-olefin is reacted with a syngas comprising hydrogen and carbon monoxide at a molar ratio of hydrogen to carbon monoxide of 1:1.

* * * * *